United States Patent
Chaptinel et al.

(10) Patent No.: US 11,154,213 B2
(45) Date of Patent: Oct. 26, 2021

(54) DETECTION OF POSITION AND FREQUENCY OF A PERIODICALLY MOVING ORGAN IN AN MRI EXAMINATION

(71) Applicants: Jérôme Chaptinel, Lausanne (CH); Robin Demesmaeker, Morges (CH); Jérôme Yerly, Charmey (CH); Tobias Kober, Lausanne (CH); Davide Piccini, Prilly (CH)

(72) Inventors: Jérôme Chaptinel, Lausanne (CH); Robin Demesmaeker, Morges (CH); Jérôme Yerly, Charmey (CH); Tobias Kober, Lausanne (CH); Davide Piccini, Prilly (CH)

(73) Assignees: CENTRE HOSPITALIER UNIVERSITAIRE VAUDOIS, Lausanne (CH); SIEMENS HEALTHCARE GMBH, Erlangen (DE)

( * ) Notice: Subject to any disclaimer, the term of this patent is extended or adjusted under 35 U.S.C. 154(b) by 534 days.

(21) Appl. No.: 15/947,360

(22) Filed: Apr. 6, 2018

(65) Prior Publication Data
US 2018/0289281 A1  Oct. 11, 2018

(30) Foreign Application Priority Data
Apr. 7, 2017 (EP) .................................... 17165544

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/0044* (2013.01); *A61B 5/02411* (2013.01);
(Continued)

(58) Field of Classification Search
CPC .............. A61B 2503/02; A61B 5/0044; A61B 5/02411; A61B 5/055; A61B 5/1107;
(Continued)

(56) References Cited

U.S. PATENT DOCUMENTS

| | | | |
|---|---|---|---|
| 5,233,516 A | 8/1993 | Le Roux | |
| 5,873,825 A * | 2/1999 | Mistretta | A61B 5/055 324/307 |

(Continued)

OTHER PUBLICATIONS

Chaptinel, J., et al. "A Golden-Angle Acquisition Coupled with kt Sparse SENSE Reconstruction for Fetal Self Retro-Gated Cine Cardiac MRI: an In Vivo Feasibility Study." Int Soc Magn Reson Med. vol. 2016. 2016.

(Continued)

*Primary Examiner* — Mark D Remaly
(74) *Attorney, Agent, or Firm* — Lempia Summerfield Katz LLC (57) ABSTRACT

A method and system are provided for detecting a position of a periodically moving organ in a MRI examination. MR images of an examining person including a periodically moving organ are provided over a plurality of periodic cycles of the periodically moving organ. Based on the provided MR images, a pixel frequency is associated with each pixel of the MR images. Using the associated pixel frequencies and the positions of the pixels within the MR images, the position and the frequency of the periodically moving organ are determined.

10 Claims, 5 Drawing Sheets

(51) Int. Cl.
| | |
|---|---|
| A61B 5/024 | (2006.01) |
| G01R 33/563 | (2006.01) |
| G01R 33/567 | (2006.01) |
| G06T 7/20 | (2017.01) |
| G01R 33/565 | (2006.01) |
| G01R 33/48 | (2006.01) |
| G01R 33/56 | (2006.01) |
| A61B 5/11 | (2006.01) |
| A61B 5/113 | (2006.01) |

(52) U.S. Cl.
CPC ... *G01R 33/5676* (2013.01); *G01R 33/56325* (2013.01); *G06T 7/20* (2013.01); *A61B 5/113* (2013.01); *A61B 5/1107* (2013.01); *A61B 5/7289* (2013.01); *A61B 2503/02* (2013.01); *G01R 33/4824* (2013.01); *G01R 33/5608* (2013.01); *G01R 33/56509* (2013.01); *G06T 2207/10088* (2013.01); *G06T 2207/30048* (2013.01)

(58) Field of Classification Search
CPC ... A61B 5/113; A61B 5/7289; G01R 33/4824; G01R 33/5608; G01R 33/56325; G01R 33/56509; G01R 33/5676; G06T 2207/10088; G06T 2207/30048; G06T 7/20
See application file for complete search history.

(56) References Cited

U.S. PATENT DOCUMENTS

| | | |
|---|---|---|
| 2007/0247150 A1 | 10/2007 | van der Kouwe |
| 2011/0178392 A1 | 7/2011 | Kuhara et al. |
| 2016/0104279 A1 | 4/2016 | Li et al. |

OTHER PUBLICATIONS

European Office Action for European Patent Application No. 17165544.2-1657, dated Oct. 12, 2017.
Feng, Li, et al. "Golden-angle radial sparse parallel MRI: Combination of compressed sensing, parallel imaging, and golden-angle radial sampling for fast and flexible dynamic volumetric MRI." Magnetic resonance in medicine 72.3 (2014): 707-717.
Feng, Li, et al. "Highly accelerated real-time cardiac cine MRI using k-t SPARSE-SENSE." Magnetic resonance in medicine 70.1 (2013): 64-74.
Hiba, Bassem, et al. "Cardiac and respiratory double self-gated cine MRI in the mouse at 7 T." Magnetic resonance in medicine 55.3 (2006): 506-513.
Kilner, Philip J., et al. "Recommendations for cardiovascular magnetic resonance in adults with congenital heart Disease from the respective working groups of the European Society of Cardiology." European heart journal 31.7 (2010): 794-805.
Larson, Andrew C., et al. "Self-gated cardiac cine MRI." Magnetic resonance in medicine 51.1 (2004): 93-102.
Liu, Jing, et al. "Respiratory and cardiac self-gated free-breathing cardiac CINE imaging with multiecho 3D hybrid radial SSFP acquisition." Magnetic resonance in medicine 63.5 (2010): 1230-1237.
Paley, Martyn NJ, et al. "Fetal electrocardiogram (fECG) gated MRI." Sensors 13.9 (2013): 11271-11279.
Pang, Jianing, et al. "ECG and navigator-free four-dimensional whole-heart coronary MRA for simultaneous visualization of cardiac anatomy and function." Magnetic resonance in medicine 72.5 (2014): 1208-1217.
Tsao, Jeffrey, Peter Boesiger, and Klaas P. Pruessmann. "k-t BLAST and k-t SENSE: Dynamic MRI with high frame rate exploiting spatiotemporal correlations." Magnetic resonance in medicine 50.5 (2003): 1031-1042.
Van Amerom, J. F. P., et al. "Fetal cardiac cine imaging from motion-corrected super-resolution reconstruction of highly-accelerated real-time MRI." Proc Int Soc Magn Reson Med. vol. 24. 2016.
Votino, Carmela, et al. "Magnetic resonance imaging in the normal fetal heart and in congenital heart disease." Ultrasound in obstetrics & gynecology 39.3 (2012): 322-329.
Wielandner, Alice, et al. "Potential of magnetic resonance for imaging the fetal heart." Seminars in Fetal and Neonatal Medicine. vol. 18. No. 5. Elsevier, 2013.
Yerly, Jérôme, et al. "Coronary endothelial function assessment using self-gated cardiac cine MRI and k-t sparse SENSE." Magnetic resonance in medicine 765 (2016): 1443-1454.
Haris K. et. al.: "Fetal Cardiac MRI with self-gated iGRASP", vol. 24, p. 3104. 2016.

* cited by examiner

DETECTION OF POSITION AND FREQUENCY OF A PERIODICALLY MOVING ORGAN IN AN MRI EXAMINATION

CROSS REFERENCE TO RELATED APPLICATIONS

This application claims the benefit of EP 17153565, filed on Jan. 27, 2017, which is hereby incorporated by reference in its entirety.

FIELD

Embodiments relate to a method for detecting a position and a frequency of a periodically moving organ in an MRI examination and a method for detecting a cardiac position and a cardiac frequency in a cardiac MRI examination.

BACKGROUND

One of the assumptions of magnetic resonance imaging (MRI) is that the object to be imaged does not move during the acquisition of the imaging data. In some MRI scan scenarios of an examining person, a continuously moving organ of the examining person is scanned, for example, the heart of an examining person, and further the fetal heart of a fetus within a maternal body is scanned. The acquisition may be synchronized with the heart activity, either by acquiring only in certain positions within the cardiac cycle or by using information on the heart activity to retrospectively mitigate the motion effects.

Cardiac self-gating, for example, is achieved by extracting a cardiac physiological signal directly form the acquired MRI data, rather than from external triggering or gating sources as performed in today's clinical routine (e.g. electrocardiogram or ECG). Although several advances have been made in recent years, the concept has not yet been translated into clinical practice. One of the biggest hurdles to clinical translation is the difficulty to extract a reliable gating signal over a wide population of different subjects and pathologies. Common method steps usually involve, for instance, the choice of the coils where such signal is expressed most clearly as disclosed in the document Larson et al. "Self-gated cardiac cine MRI.", Magn Reson Med. 51(1): 93-102 (2004), the selection of the precise peak of the cardiac frequency amongst a wide frequency spectrum as disclosed in the cited prior art document Pang et al., "ECG and navigator-free four-dimensional whole-heart coronary MRA for simultaneous visualization of cardiac anatomy and function.", Magn Reson Med. 72(5): 1208-1217 (2014), and, in algorithms that involve the extraction of the signal from image series, the manual segmentation of a region of interest encompassing the heart as disclosed in the document Chaptinel et al. "A Golden-Angle Acquisition Coupled with K-T Sparse SENSE Reconstruction for Fetal Self Retro-Gated Cine Cardiac MRI: An in Vivo Feasibility Study." ISMRM 24: 459 (2016).

While in many cases it is possible to make use of an external ECG signal, a field that exemplifies the need of cardiac self-gating in clinical practice and that is perhaps also one of the most challenging is fetal cardiac imaging. Congenital heart disease (CHD) has an incidence of about 4-13 occurrences per 1000 live births and is currently a leading cause of infant mortality. Prenatal detection of CHD allows in-utero referral to tertiary care centers, that plays an important role in improving perinatal care. Fetal echocardiography (echo) is an easily accessible real-time technique and provides a relatively high sensitivity for detecting major CHD during second-trimester screening programs as disclosed in the document Votino et al. "Magnetic resonance imaging in the normal fetal heart and in congenital heart disease." Ultrasound Obstet Gynecol. 39(3), 322-329, (2012). However, fetal echocardiography is occasionally limited by acoustic window, poor images of the distal vasculature, fetal position, maternal adipose tissue, abdominal wall scar form previous abdominal or pelvic surgery, and is highly user dependent. Such factors, however, do not necessarily compromise the image quality of magnetic resonance imaging. MRI therefore may be applied in the second and third trimesters, to avoid any risk during organogenesis, as a complementary modality when the diagnosis by echo may be uncertain and is already becoming part of the clinical routine in various centers as disclosed in the document Wielandner et al. "Potential of magnetic resonance for imaging the fetal heart." Seminars in Fetal Neonatal Medicine, 18 286-297 (2013).

As described above, MRI is based on the assumption that the object to be imaged does not move during the acquisition time, e.g. that all data collected during one single acquisition are spatially consistent. Consequently, the two major challenges in fetal cardiac MRI are the lack of an external ECG signal that may be used to synchronize data acquisition with the fetus' heartbeat and the unpredictable and spontaneous fetal motion that makes the planning of the scan very complicated and cumbersome. Moreover, the heart of the fetus is a relatively small structure within a very large and moving field-of-view (FOV)—the mother, who is breathing during the examination and it is not possible to rely on a standard adult cardiac image orientations planning, for example views of 2, 3 or 4 cardiac chambers as disclosed in the document Kilner et al. "Recommendations for cardiovascular magnetic resonance in adults with congenital heart disease from the respective working groups of the European Society of Cardiology." Eur Heart J. 31: 794-805 (2010), as the position of the fetus within the FOV is varying constantly and unpredictably.

Besides a minority of studies that focus on trying to use an external signal for cardiac triggering and gating in fetal cardiac MRI, as disclosed in the document Paley et al. "Fetal Electrocardiogram (fECG) Gated MRI." Sensors, 13 11271-11279 (2013), most of the recent advances make use of self-gating techniques that do not require the use of an external device. Examples of the techniques are disclosed in the documents Van Amerom et al. "Fetal cardiac cine imaging from motion-corrected super-resolution reconstruction of highly accelerated real-time MRI." ISMRM 24: 458 (2016) and Haris et al. "Fetal Cardiac MRI with self-gated iGRASP." ISMRM 24: 3104 (2016).

The methods make use of fast and flexible MRI acquisition schemes, as well as a three-step reconstruction technique as for example disclosed in the document Yerly J et al. "Coronary endothelial function assessment using self-gated cardiac cine MRI and k-t sparse SENSE." Magn. Reson. Med. 76 (5), 1443-1454 (2015). Within the three-step reconstruction, the first step includes producing a series of images over several heartbeats (e.g. usually acquired in a single maternal breath-hold, and often referred to as real-time reconstruction) with high temporal resolution, but also highly undersampled (e.g. with suboptimal image quality). The temporal series of images is used to extract a cardiac gating signal through self-gating in the second step. In the third and final step, the gating signal is used to retro-gate the acquired data into a single cardiac cycle. The final reconstruction uses the gating signal to group data from different heartbeats into one single heartbeat according to the cardiac phase to which the data belong.

As mentioned above, to achieve the three-step reconstruction approach, the MRI acquisition should be fast (to achieve high temporal resolution in the first reconstruction step) and flexible (to be able to retro-gate or re-sort the data for the final reconstruction). The acquisition schemes are based on a continuous golden-angle acquisition or on alternative sampling patterns, as disclosed for example in the document Yerly J et al. "Coronary endothelial function assessment using self-gated cardiac cine MRI and k-t sparse SENSE." Magn Reson Med. 76 (5), 1443-1454 (2015), while all steps of the reconstruction involve enhanced reconstruction techniques, such as GRASP, as disclosed for example in the document Feng et al. "Golden-Angle Radial Sparse Parallel MRI: Combination of Compressed Sensing, Parallel Imaging, and Golden-Angle Radial Sampling for Fast and Flexible Dynamic Volumetric MRI." Magn Reson Med., 72: 707-717 (2014), or k-t sparse SENSE, as disclosed for example in the document Feng et al. "Highly accelerated real-time cardiac cine MRI using k-t SPARSE-SENSE." Magn Reson Med., 70(1):64-74 (2013).

BRIEF SUMMARY

The scope of the present invention is defined solely by the appended claims and is not affected to any degree by the statements within this summary. The present embodiments may obviate one or more of the drawbacks or limitations in the related art.

Embodiments are provided for an improved, more robust and more reliable self-gating method for an MRI examination of a periodically moving organ, where a clear and precise self-gating signal is provided and a method for detecting a position and a frequency of a periodically moving organ in an MRI examination.

In an embodiment, a method for detecting a position of a periodically moving organ in a MRI examination is provided. The method includes providing a plurality of MR images of an examining region including a periodically moving organ over a plurality of periodic cycles. Each MR image is a magnitude image and contains a plurality of pixels. The method further includes associating a pixel frequency to each of the plurality of pixels based on the plurality of MR images, determining a position of each pixel within the plurality of MR images, and detecting the position of the periodically moving organ based on the pixel frequencies associated to each pixel and based on the position of the pixels within the plurality of MR images.

By associating a pixel frequency to each of the plurality of pixels and detecting the position of a periodically moving organ based on the pixel frequencies, the position of the periodically moving organ is more reliably and precisely detected. Regardless of the different anatomy, position, and orientation of the MR images, for example different views of the body of an examining person, different views of the periodically moving organ, and—in the case of a fetal heart—additionally different positions of the fetus within the maternal body, the method reliably and precisely localizes the position and frequency of the periodically moving organ.

The method may further include determining an organ frequency of the periodically moving organ based on the detected position. By determining the organ frequency of the periodically moving based on the detected organ position, a clear and precise self-gating signal is extracted, that may be used for an image reconstruction process.

The method may further include filtering MR images to generate filtered magnitude images that are spatially smoothed MR magnitude images. By filtering the MR images, the quality of the MR images is improved and the method is made more robust.

The MR images may be provided based on MR signals from the examining region, and the method may further include determining a phase evolution of the MR signals over time for the plurality of pixels, discarding pixels in provided MR images whose phase value over time has a variation larger than a phase threshold, and generating a frequency mask in which discarded pixels are removed of the MR image. By discarding pixels in the provided MR images, whose phase value over time has a variation larger than a phase threshold, streaking artefacts are removed from the MR images. The quality of the MR images is improved resulting in more robust and precise results of the method.

The filtered magnitude images may be masked with the frequency mask to obtain masked magnitude images. By masking the filtered magnitude images with the frequency mask, image quality is further improved and, therefore, the method provides improved robust and precise results.

The method may further include transforming the MR images into frequency space and filtering out all frequencies outside a predefined frequency range. Filtering out all frequencies outside a predefined frequency range leads to improved results and preciseness of the results of the method, as irrelevant frequencies, that do not correspond to a frequency range typical for the organ, are not taken into account. As the frequency range of a fetal heart is known, all frequencies outside the range may be filtered out.

The masked magnitude images may be transformed into frequency space. By transforming the masked magnitude images into frequency space, the robustness preciseness of the method further improved.

The position of the periodically moving organ may be detected based on the biggest group of pixels that include substantially the same pixel frequency. Basing the detection of the position of the periodically moving organ on the biggest group of pixels that include substantially the same pixel frequency, improves robustness preciseness of the method by reliably determining on pixels that are associated with an area of the periodically moving organ in the MR images.

Based on the assumption that the periodically moving organ is the object of the examination and, therefore, placed around the center of the FOV, the position of the periodically moving organ may be detected based on the biggest group of pixels, whose distance from the center of the MR images is within a spatial threshold. Taking into account only a group of pixels that is within a spatial threshold of the center of the MR images further improves robustness and preciseness of the method by not considering groups of pixels that are near the image borders, therefore may not be not associated with the periodically moving organ.

Associating a pixel frequency to each of the plurality of pixels may include creating a frequency map. Each pixel is associated with a most significant frequency of its frequency space. The creation of the frequency map provides for graphical display of the groups of pixels to a user, and further provides for the use of image processing techniques on the frequency map that improves robustness and preciseness of the method.

In an embodiment, a computing device is provided that is configured to detect a position of a periodically moving organ in a MRI examination. The computing device may include a memory and at least one processor, the memory containing instructions by the at least one processor. The computing device is configured for receiving a plurality of MR images of an examining region including a periodically moving organ over a plurality of periodic cycles. Each MR image is a magnitude image and contains a plurality of pixels. Further, the computing device is configured for associating a pixel frequency to each of the plurality of pixels based on the plurality of MR images, determining a position of each pixel within the plurality of MR images, and detecting the position of the periodically moving organ based on the pixel frequencies associated to each pixel and based on the position of the pixels within the plurality of MR images.

By associating a pixel frequency to each of the plurality of pixels and detecting an organ position based on the pixel frequencies, the computing device is configured to detect the position of the periodically moving organ is reliably and precise, thereby operating in a robust way.

The computing device may be further configured for determining an organ frequency of the periodically moving organ based on the detected position. By determining the organ frequency of the periodically moving based on the detected organ position, a clear and precise self-gating signal is extracted, that may be used for an image reconstruction process.

In an embodiment, a computer program is provided, that includes program code to be executed by at least one processor of a computing device. The execution of the program code causes the at least one processor to execute a method according to any of the methods described above.

In an embodiment, a MR imaging system is provided, that is configured to detect a position of a periodically moving organ in a MRI examination. The MR imaging system includes a control unit that includes a computing device with a memory and at least one processor, the memory contains instructions by the at least one processor, and the computing device is configured for receiving a plurality of MR images of an examining region including a periodically moving organ over a plurality of periodic cycles. Each MR image is a magnitude image and contains a plurality of pixels. Further, the computing device is operative for associating a pixel frequency to each of the plurality of pixels based on the plurality of MR images, determining a position of each pixel within the plurality of MR images, and detecting the position of the periodically moving organ based on the pixel frequencies associated to each pixel and based on the position of the pixels within the plurality of MR images.

The MR imaging system may be further configured for determining an organ frequency of the periodically moving organ based on the detected position as described above. By determining the organ frequency of the periodically moving based on the detected organ position, a clear and precise self-gating signal is extracted, that may be used for an image reconstruction process.

DETAILED DESCRIPTION

Figure 1:
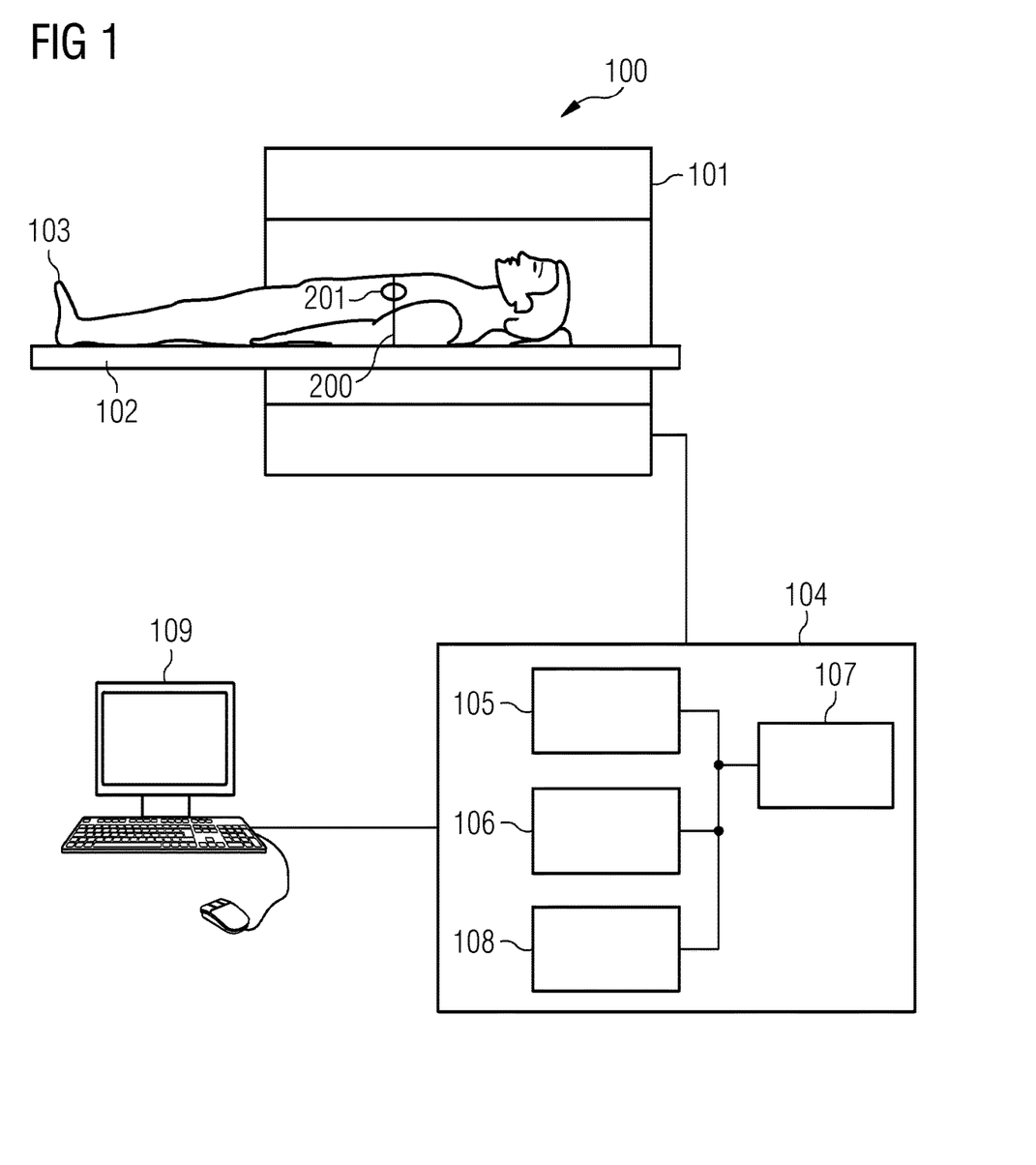
FIG. 1 schematically depicts an MR imaging system according to an embodiment.

FIG. 1 schematically depicts an MR imaging system according to an embodiment. An MR imaging system 100 with which a position and a frequency of a periodically moving organ may be determined in a MR examination is depicted in FIG. 1. The MR imaging system 100 includes a basic field magnet 101 that generates a polarization field BO. An examination person 103 arranged on a bed 102 is driven into the center of the basic field magnet 101 where the acquisition of the MR signals from an examination region 200 including a periodically moving organ 201 is implemented via radiation of RF pulses and switching of gradients. How MR images 300—for example, images of multi-gradient echo sequences—may be generated in a pulse sequence with a series of RF pulses and switching of gradients is known to those skilled in the art is not described in detail herein.

The MR imaging system 100 is connected with a central control unit 104 with which the MR system 100 is controlled. The central control unit 104 includes an RF control unit 105 that controls the switching of the RF pulses to excite the magnetization. A gradient control unit 106 controls the switching of the gradient magnetic fields for spatial coding of the excited spins. An imaging acquisition unit 107 controls the workflow of the gradient switching, the RF pulses, and the MR signal readout depending on the selected imaging sequence.

A computing device 108 processes MR signals and calculates MR images 300 and phase evolutions 500 of the MR signals via Fourier transformation from the MR signals detected with a coil (not shown). The images and evolutions may be displayed on a display unit 109. The MR imaging system 100 may be controlled by an operator. The other typical components of an MR system have been omitted for clarity. The method described in the following in connection with FIG. 1 may for example be implemented with the aid of the computing device 108 or a processing unit integrated into the display unit 109.

Figure 2:
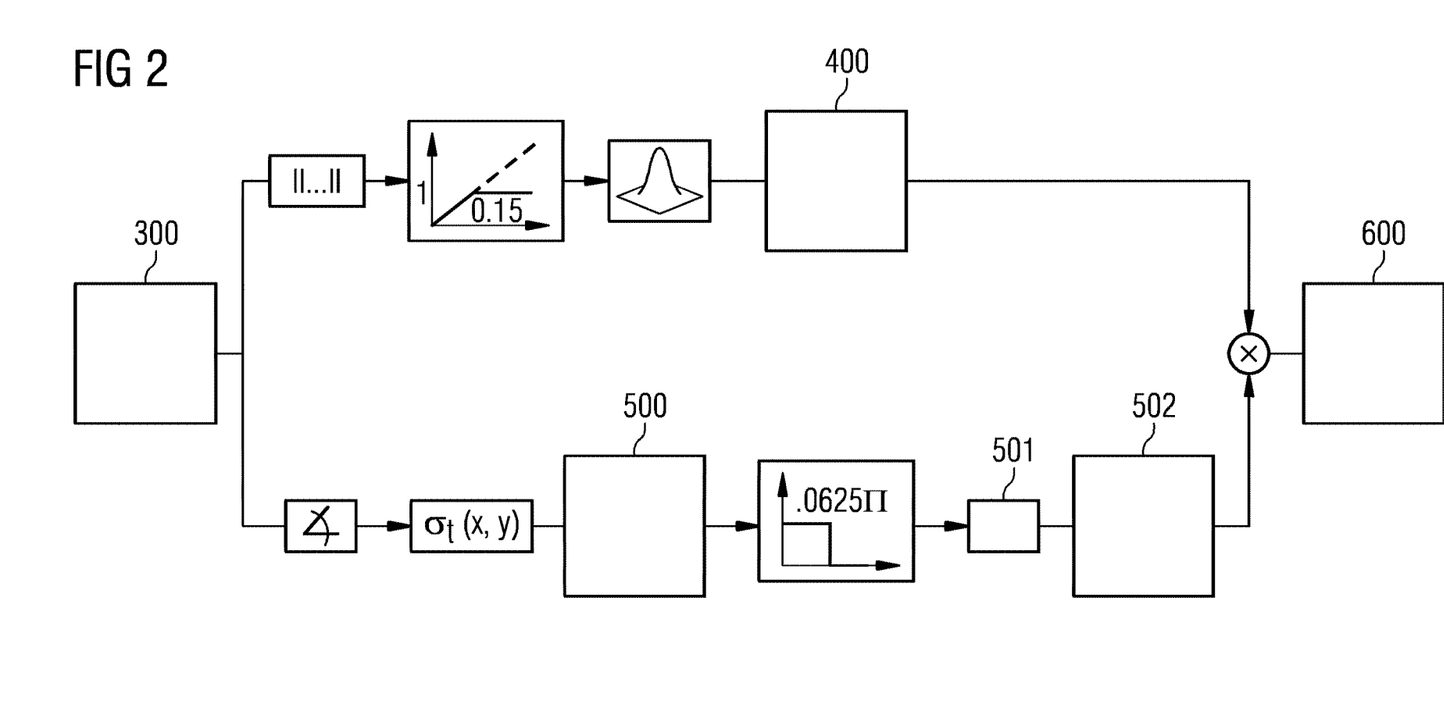
FIG. 2 depicts a first part of a flow chart of a method for detecting position and frequency of a periodically moving organ in an MRI examination according to an embodiment.

FIG. 2 depicts a first part of a flow chart of the method for detecting position and frequency of a periodically moving organ in an MRI examination according to an embodiment.

In an embodiment, a position and a frequency of a fetal heart are automatically localized using a combination of both spatial and temporal features. The fetal heart is assumed to be roughly in the center of the Field-Of-View (FOV) and the fetal cardiac frequency range between 110 and 180 bpm, while being constant during the usually short acquisition time, for example, one single maternal breath-hold.

In an act, a plurality of MR images 300 of an examining region 200 including a fetal heart 201 over a plurality of periodic cycles are provided. The MR images 300 are magnitude images and contain a plurality of pixels.

The imaging sequence used for this embodiment is a 2D radial acquisition using a continuous golden angle displacement between subsequent readouts. The acquisition provides high spatial uniformity over time as well as the possibility to reorder the readouts according to the extracted periodic signal. Lastly, golden angle acquisitions provide the pseudo-randomness needed to achieve a good reconstruction quality in the three-step reconstruction mentioned above. Any other acquisition scheme (e.g. Cartesian, radial, spiral, etc) that has the characteristics may also be used.

In a following act, the magnitude image series is saturated and spatially smoothed, for example by a Gaussian filter with width of two pixels, to enhance the signal from blood and fat, thereby creating filtered magnitude images.

However, streaking artifacts stemming from the radial acquisition scheme also appear in the frequency range of the fetal heart. Therefore, to mask out probable streaking artifacts, in a parallel act, a frequency mask 502 is created from phase evolutions of the MR signals. Phase evolutions 500 of each MR image 300 are generated, and pixels including a standard deviation over the time series in the phase images larger than a threshold are discarded. Thereafter, mathematical morphology operations 501 are performed on the resulting frequency mask 502, to improve the performance and quality of the method. For example, opening/closing operations that eliminate small, unconnected patches of the frequency mask 502 are performed.

The filtered magnitude images 400 may be masked by frequency mask 502 discarding all pixels with standard deviation over the time series in the phase images larger than e.g. pi/16, in order to filter out pixels containing streaking image artefacts. The result of the masking operation are masked magnitude images 600.

Figure 3:
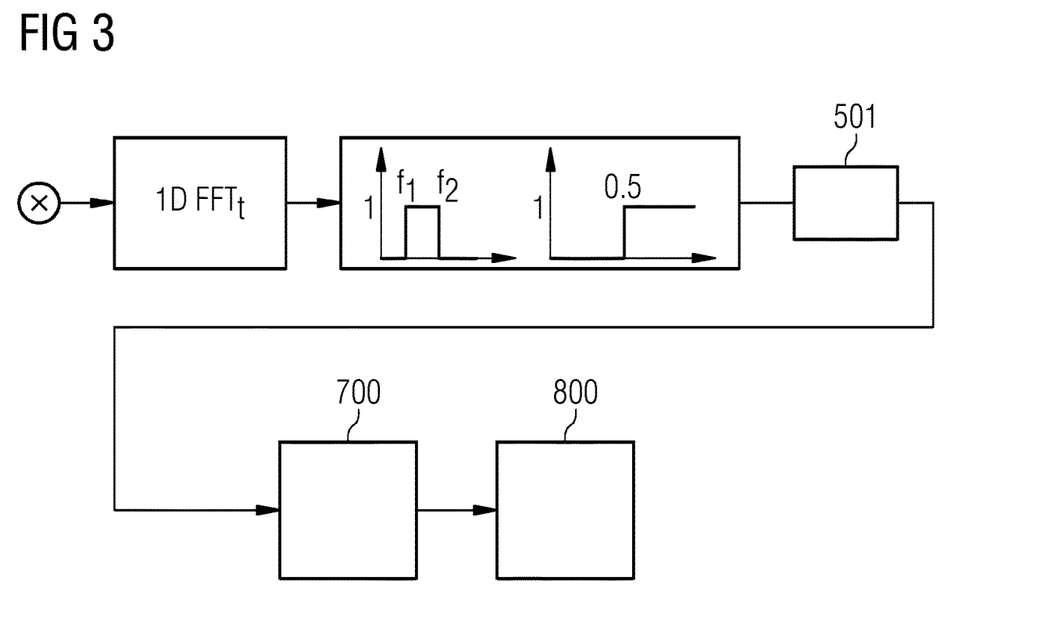
FIG. 3 depicts a second part of a flow chart of the method for detecting position and frequency of a periodically moving organ in an MRI examination according to an embodiment.

FIG. 3 depicts a second part of a flow chart of the method for detecting position and frequency of a periodically moving organ in an MRI examination according to an embodiment.

The position of the fetal heart is detected by 1D Fourier transforming the pixel signal variations of masked magnitude images 600 over time. A pixel signal variation over time for each of the plurality of pixels is determined. Each pixel signal value of the respective pixel is a signal value of the respective pixel in one of the masked magnitude images 600. The pixel signal variation over time is defined by the variation of the signal value of a pixel from image to image. A 1D-Fourier-Transformation of each pixel signal variation over time is performed, resulting in a frequency spectrum of each pixel. A thresholding process is performed on each frequency spectrum, to discard frequencies outside of a defined frequency range, that corresponds to a frequency range typical for the periodically moving organ. The frequency spectrum of each pixel exhibits a peak within the predefined frequency range that may be correlated to the fetal heart frequency to be determined.

A frequency is associated to each pixel. The frequency corresponds to the peak within the predefined frequency range, e.g. the frequency with the highest signal based on the results of the 1D Fourier-Transformation of the respective pixel signal variation over time. The frequency with the highest signal, or the most significant frequency in the respective frequency spectrum within the predefined frequency range is assigned to each pixel. A frequency map is created.

The position of the fetal heart 201 is detected based on the pixel frequencies associated to each pixel and based on the position of the pixels within the plurality of MR images 300.

A group of pixels is selected. All pixels within the group have substantially the same pixel frequency. The frequency is within the predetermined frequency range and the group of pixels is closest to the center of the MR images 600 and the frequency map. In an embodiment, the group of pixels is within a spatial threshold from the center and in another embodiment selected based on its distance to the center of the MR images 300.

Mathematical morphology operations 501 are performed on the selected group of pixels. For example, dilation operations are performed, to make the contours of the group of pixels bigger and more regular.

The selected group of pixels may be referred to as anatomical mask 700 of the fetal heart 201 and corresponds to the position of the fetal heart 201 in the MR images 300.

An organ frequency 800 of the fetal heart is extracted based on the anatomical mask 700 by performing an accurate frequency estimate based on the pixel signal variations over time in the masked magnitude images 600 of all pixels contained in the anatomical mask 700.

As the frequency resolution is limited by the FFT spacing, e.g. by the temporal resolution of the MR images 300, the Fourier frequency corresponding to the selected anatomical mask 700, as described above, provides only a rough estimate for the true organ frequency. A subsequent least-square fitting of the pixel signal variations over time within this mask with frequencies close to the rough estimate value provides the final and more accurate estimate of the organ frequency 800 of the fetal heart 201.

Figure 4:
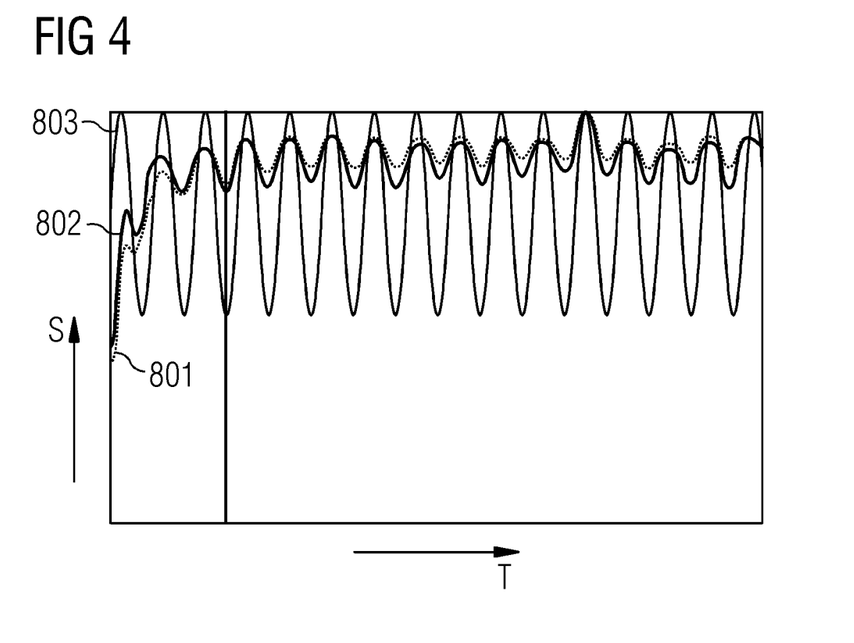
FIG. 4 depicts frequency signals for a periodically moving organ derived by the method according to an embodiment compared to conventional methods derived from MR images with high quality.

FIG. 4 depicts frequency signals for a fetal heart 201 derived by the method according to an embodiment compared to conventional methods, derived from MR images 300 with high quality.

Figure 5:
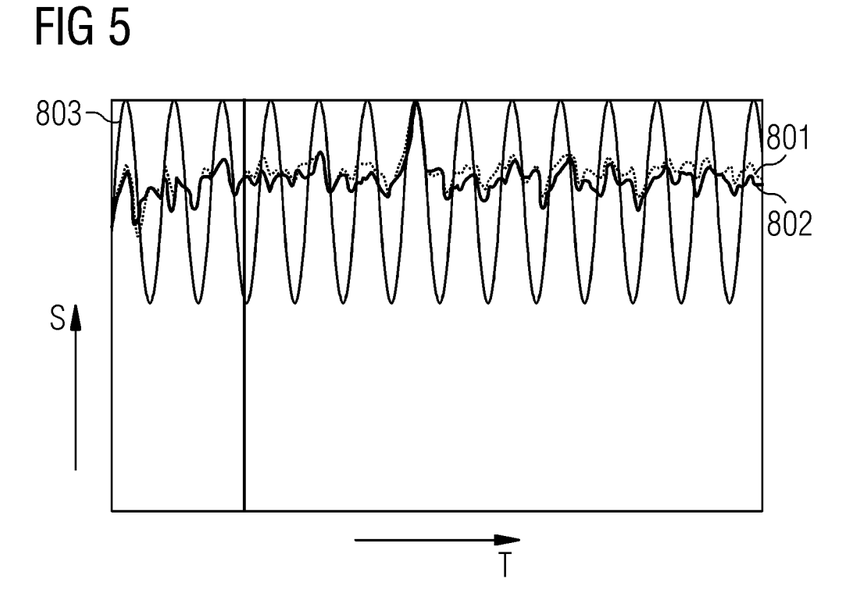
FIG. 5 depicts frequency signals for a periodically moving organ derived by the method according to an embodiment compared to conventional methods derived from MR images with low quality.

FIG. 5 depicts frequency signals for a fetal heart derived by the method according to an embodiment compared to conventional methods, derived from MR images 300 with low quality.

In FIG. 4 and FIG. 5, Frequency signal 801 is obtained with a conventional automated segmentation and cross-correlation (black dotted line). Frequency signal 802 is obtained with a manual segmentation and Pearson cross-correlation (black continuous line). Frequency signal 803 is obtained with the method according to an embodiment (black continuous line).

In FIG. 4, an example of good quality real-time images, cross-correlation detects a reliable cardiac signal in both cases (conventional automated mask 801 and conventional manual mask 802) with high correlation between the two. The frequency detection according to an embodiment estimates a sinusoidal signal 803 that is also highly correlated with the other two.

In FIG. 5, an example of real-time images with low quality, conventional cross-correlation does not reliably detect the cardiac gating signal. The two cross-correlation signals 801 and 802 are still visually highly correlated, but extremely noisy. The frequency detection according to an embodiment, however, still estimates a reliable sinusoidal signal 803 in the difficult scenario as well.

Figure 6:
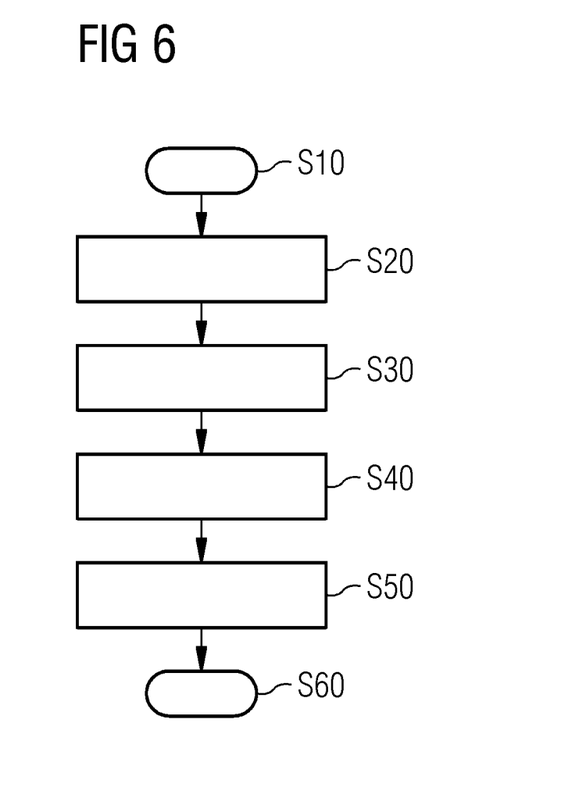
FIG. 6 depicts a flow chart of the method for detecting position and frequency of a periodically moving organ in an MRI examination according to an embodiment.

FIG. 6 depicts a flow chart of the method for detecting position and frequency of a periodically moving organ in an MRI examination according to an embodiment.

The method starts with act S10. At act S20, a plurality of MR images 300 of an examining region 200 including a periodically moving organ 201 over a plurality of periodic cycles are provided. Each MR image 300 is a magnitude image and contains a plurality of pixels. The MR images 300 provide a high-temporal resolution and a highly undersampled reconstruction that is also referred to as real time images and real-time reconstruction. The periodically moving organ 201 may for example be the heart of an examining person, or a fetal heart of a fetus within the examining person. The described method may be extended to different patient populations, e.g. in adults, adolescents and infants. Different cardiac frequency ranges and spatial artifacts may be considered in the different patient populations.

At act S30, a pixel frequency is associated to each of the plurality of pixels based on the plurality of on MR images 300.

At act S40, a position of each pixel within the plurality of MR images 300 is determined.

At act S50, the position of the periodically moving organ 201 is detected based on the pixel frequencies associated to each pixel and based on the position of the pixels within the plurality of MR images. The method ends with act S60.

In an embodiment, in a field of MRI, a method is provided for the detection of a position and a frequency of a periodically moving organ 201, for example, for detecting a fetal cardiac gating signal (fetal cardiac self-gating). A cardiac mask is extracted from real-time cine fetal images that makes use both of the time-frequency and the spatial domain. The effectiveness of the presented embodiments are proven against the published "gold standard" manual segmentation and reference cardiac phase selection. Variations of the automated detection algorithm may be needed to adapt it to a different kind of acquisition scheme (e.g. Cartesian or spiral VS radial) or to a different type of "real time" cine reconstruction (e.g. k-t sparse SENSE VS a different advanced reconstruction technique).

It is to be understood that the elements and features recited in the appended claims may be combined in different ways to produce new claims that likewise fall within the scope of the present invention. Thus, whereas the dependent claims appended below depend from only a single independent or dependent claim, it is to be understood that the dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for detecting a position of a periodically moving organ in a magnetic resonance imaging (MRI) examination, the method comprising:
providing a plurality of magnetic resonance (MR) images of an examining region comprising a periodically moving organ over a plurality of periodic cycles, wherein each MR image of the plurality of MR images is a magnitude image and comprises a plurality of pixels each pixel including a location and a pixel signal value representative of an amplitude of an MR signal;
determining a pixel signal variation over time for each pixel of the plurality of pixels over the plurality of MR images, wherein the pixel signal variation over time is the variation of the pixel signal value of equally located pixels from MR image to MR image of the plurality of MR images;
transforming, using a 1D Fourier-transformation the pixel signal variations over time into a frequency spectrum;
associating a pixel frequency with each pixel, the pixel frequency comprising a highest signal for each pixel from a respective frequency spectrum of each pixel;
determining a position of each pixel within the plurality of MR images; and
detecting the position of the periodically moving organ based on the pixel frequency associated with each pixel of the plurality of pixels and based on the positions of the plurality of pixels within the plurality of MR images.

2. The method of claim 1, further comprising:
determining an organ frequency of the periodically moving organ based on the detected position.

3. The method of claim 1, further comprising:
generating filtered magnitude images that are spatially smoothed MR magnitude images, the generating of the filtered magnitude images comprising filtering the plurality of MR images.

4. The method of claim 1, wherein providing the plurality of MR images comprises providing the plurality of MR images based on MR signals from the examining region, wherein the method further comprises:
determining a phase evolution of the MR signals over time for the plurality of pixels;
discarding pixels having a phase value over time that has a variation larger than a phase threshold in the plurality of provided MR images; and
generating a frequency mask in which discarded pixels are removed from the MR image.

5. The method of claim 4, further comprising obtaining masked magnitude images, the obtaining of the masked magnitude images comprising masking the filtered magnitude images with the frequency mask.

6. The method of claim 5, further comprising:
transforming the plurality of MR images into frequency space and filtering out all frequencies outside a predefined frequency range.

7. The method of claim 6, wherein the masked magnitude images are transformed into frequency space.

8. The method of claim 1, wherein the position of the periodically moving organ is detected based on a biggest group of pixels that includes a same pixel frequency.

9. The method of claim 1, wherein the position of the periodically moving organ is detected based on a biggest group of pixels with a distance from a center of the plurality of MR images that is within a spatial threshold.

10. The method of claim 1, wherein associating a pixel frequency with each pixel of the plurality of pixels comprises creating an anatomical frequency map, and
wherein each pixel is associated with a most significant frequency of a frequency space of the respective pixel.

* * * * *